US009365660B2

(12) United States Patent
Yan et al.

(10) Patent No.: US 9,365,660 B2
(45) Date of Patent: Jun. 14, 2016

(54) ANIONIC POLYMERIZATION INITIATORS AND PROCESSES

(75) Inventors: Yuan-Yong Yan, Copley, OH (US); Zengquan Qin, Copley, OH (US); Xiao-Dong Pan, Akron, OH (US); David M. Roggeman, North Royalton, OH (US)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 13/381,311

(22) PCT Filed: Jun. 28, 2010

(86) PCT No.: PCT/US2010/040242

§ 371 (c)(1),
(2), (4) Date: Feb. 8, 2012

(87) PCT Pub. No.: WO2011/008501

PCT Pub. Date: Jan. 20, 2011

(65) Prior Publication Data

US 2012/0136128 A1 May 31, 2012

Related U.S. Application Data

(60) Provisional application No. 61/221,622, filed on Jun. 30, 2009.

(51) Int. Cl.

| | |
|---|---|
| ***C08F 4/48*** | (2006.01) |
| ***C07F 1/02*** | (2006.01) |
| ***C08F 36/04*** | (2006.01) |
| *C08F 136/04* | (2006.01) |
| *C08F 236/04* | (2006.01) |
| *C08F 12/08* | (2006.01) |

(52) U.S. Cl.

CPC ... *C08F 4/48* (2013.01); *C07F 1/02* (2013.01); *C08F 4/484* (2013.01); *C08F 36/04* (2013.01); *C08F 12/08* (2013.01); *C08F 136/04* (2013.01); *C08F 236/04* (2013.01); *C08F 2810/40* (2013.01)

(58) Field of Classification Search

CPC .................. C08F 12/314; C08F 12/08; C08F 236/00–236/22; C08F 136/00–136/22; C08F 2810/40; C08F 4/48; C08F 4/484

USPC .............................................. 526/173, 347.1

See application file for complete search history.

(56) References Cited

U.S. PATENT DOCUMENTS

| | | | | |
|---|---|---|---|---|
| 3,872,108 | A * | 3/1975 | Ukyo et al. | 549/401 |
| 4,158,098 | A * | 6/1979 | Trepka | 568/633 |
| 4,499,243 | A | 2/1985 | Rader | |
| 4,725,654 | A * | 2/1988 | Priddy et al. | 526/60 |
| 5,219,681 | A | 6/1993 | Yamada et al. | |
| 5,336,726 | A * | 8/1994 | DuBois | 525/272 |
| 5,717,015 | A | 2/1998 | Dust et al. | |
| 6,770,201 | B2 * | 8/2004 | Shepodd et al. | 210/635 |
| 7,056,985 | B2 | 6/2006 | Faust et al. | |
| 7,208,171 | B2 | 4/2007 | Messersmith et al. | |
| 7,226,979 | B2 | 6/2007 | Faust et al. | |
| 2003/0216522 | A1 | 11/2003 | Oshima et al. | |
| 2010/0286348 | A1 | 11/2010 | Pan et al. | |
| 2011/0028632 | A1 | 2/2011 | Qin et al. | |
| 2012/0130009 | A1 | 5/2012 | Qin et al. | |
| 2012/0136113 | A1 | 5/2012 | Yan et al. | |
| 2013/0035437 | A1 | 2/2013 | Pan et al. | |

FOREIGN PATENT DOCUMENTS

| | | | |
|---|---|---|---|
| EP | 0442068 | A2 | 8/1991 |
| EP | 0455191 | A2 | 11/1991 |
| JP | 49-41116 | | 11/1974 |
| JP | 1992-053807 | A | 2/1992 |
| JP | 05-230126 | H | 9/1993 |
| JP | 07-258476 | H | 10/1995 |
| JP | 3057508 | B2 * | 6/2000 |
| JP | 2007-211054 | | 8/2007 |

OTHER PUBLICATIONS

Geerts, J. et al. "Anionic polymerization of o- and p-Methoxystyrene", 1969, Journal of Polymer Science Part A-1 vol. 7 2859-2873.*

G. Westwood et al., "Simplified Polymer Mimics of Cross-Linking Adhesive Proteins," Macromolecules, May 4, 2007, pp. 3960-3964, 2007, 40 (American Chem. Soc.; Washington, DC).

S. Ganguly et al., "Effect of surface modification of carbon black of 1,2-dihydroxy benzene and 1,2,3-trihydroxy benzene on a natural rubber-carbon black composite," Indian J. Chem. Technol., 2005, pp. 695-700, vol. 12, No. .6 (Council of Scientific & Industrial Research; New Delhi, India)—abstract only.

A. Banerjee, "Novel approach of rubber-filler interaction through surface modification of carbon black," version of article appearing in Apr. 2003 Rubber World Magazine (article downloaded from thefreelibrary.com).

A. Hirao et al., "Polymerization of Monomers Containing Functional Groups Protected by Trialkylsilyl Groups, 1-Synthesis of Poly(40vinylphenol) by Means of Anionic Living Polymerization," Makromol. Chem. Rapid Commun., 1982, 3, pp. 941-946 (Wiley-VCH; Weinheim, Germany).

(Continued)

*Primary Examiner* — Ling Choi
*Assistant Examiner* — David L Miller
(74) *Attorney, Agent, or Firm* — Meredith E. Hooker; David G. Burleson

(57) ABSTRACT

A group of compounds defined by the general formula (I) can be used to anionically initiate polymerization of unsaturated monomers. In the formula, M is an alkali metal atom, $R^1$ is an aryl group having at least one $OR^2$ substituent group where each $R^2$ is a group that is nonreactive toward M, and R is a hydrocarbyl group. The subject initiators can be used in semi-batch and continuous polymerization processes, even those which are performed at elevated temperatures.

14 Claims, No Drawings

(56) References Cited

OTHER PUBLICATIONS

K. Jankova, "Synthesis by ATRP of poly(ethylene-co-butylene)-block-polystyrene, poly(ethylene-co-butylene)-block-poly(4-acetoxystyrene) and its hydrolysis product poly(ethylene-co-butylene)-block-poly(hydroxystyrene)," Macromol. Rapid Commun., 1999, 20, pp. 219-223 (Wiley-VCH Verlag GmbH; Weinheim, Germany).
K. Satoh et al., "Direct Living Cationic Polymerization of p-Hydroxystyrene with Boron Trifluoride Etherate in the Presence of Water," Macromolecules, Jul. 8, 2000, pp. 5405-5410, 2000, 33 (American Chem. Society; Washington, DC).
M. Yu et al., :"Role of L-3,4-Dihydroxyphenylalanine in Mussel Adhesive Proteins," J. Am. Chem. Soc., 1999, 121, pp. 5825-5826 (American Chem. Soc.; Washington, DC).
D.M. Weisberg et al., "Synthesis and Characterization of Amphiphilic Poly(urethaneurea)-comb-polyisobutylene Copolymers," Macromolecules, 2000, 33, pp. 4380-4389 (American Chem. Society; Washington, DC).
A. Hirao et al., "Recent advance in living anionic polymerization of functionalized styrene derivatives," Prog. Polym. Sci., 2002, vol. 27, pp. 1399-1471 (Elsevier Science Ltd.; London, UK).
H. Lee et al., "Single-molecule mechanics of mussel adhesion," PNAS, 2006, vol. 103, No. 35, pp. 12999-13003 (The Nat'l Acad. of Sciences of the USA; Washington, DC).
K. Satoh et al., "A Linear Lignin Analogue: Phenolic Alternating Copolymers from Naturally Occurring beta-Methylstyrene via Aqueous-Controlled Cationic Copolymerization," J. Am. Chem. Soc., 2007, 129, pp. 9586-9587 (American Chem. Society; Washington, DC).
H. Lee et al., "A reversible wet/dry adhesive inspired by mussels and geckos," Nature, Jul. 19, 2007, vol. 448, pp. 338-342 (Nature Publishing Group; New York, NY).
R. Quirk et al., "Anionic synthesis of chain-end functionalized polymers using 1,1-diphenylethylene derivatives. Preparation of 4-hydroxyphenyl-terminated polystyrenes," Makromol. Chem., 1989, 190, pp. 487-493 (Wiley-VCH; Weinheim, Germany).
R. Quirk et al., "Recent Advances in the Anionic Synthesis of Chain-End Functionalized Polymers," Macromol. Symp., 2003, 195, pp. 69-74 (Wiley-VCH Verlag GmbH & KGaA; Weinheim, Germany).
International Search Report and Written Opinion in int'l appl. No. PCT/US2010/040242 (Feb. 10, 2011), 9 pp.
SIPO official action in corresponding CN national stage entry application, action dated Aug. 19, 2013—8 pp., plus 11 pp. translation.
SIPO action in CN appl. No. 201080038722.6, mailed Oct. 29, 2014—5 pp. + translation.
S. Nakahama et al., "Preparation of Tailor-Made Functional Polymers by Anionic Living Polymerization," J. Syn. Org. Chem., Japan, vol. 44-2, pp. 137-148 (Tokyo, Japan; 1986), including translation of section 2.
SIPO official action in corresponding CN national stage entry application, dated May 9, 2013—5 pp., plus 8 pp. translation.
JPO official action in corresponding JP national stage entry application, dated Jun. 10, 2014—4 pp., plus 4 pp. translation.
EPO extended search report in corresponding EP national stage entry application, dated Jun. 25, 2014—6 pp.
JPO action in JP appl. No. 2012-518567, mailed Feb. 24, 2015—3 pp. + 2-pg. translation.

* cited by examiner

ANIONIC POLYMERIZATION INITIATORS AND PROCESSES

CROSS-REFERENCE TO RELATED APPLICATIONS

This is a national stage filing under 35 U.S.C. §371 of international application no. PCT/US2010/040242, filed 28 Jun. 2010, which claimed priority to and the benefit of U.S. provisional patent appl. No. 61/221,622 filed 30 Jun. 2009.

BACKGROUND INFORMATION

Good traction and resistance to abrasion are primary considerations for tire treads; however, motor vehicle fuel efficiency concerns argue for a minimization in their rolling resistance, which correlates with a reduction in hysteresis and heat build-up during operation of the tire. These considerations are, to a great extent, competing and somewhat contradictory: treads made from compositions designed to provide good road traction usually exhibit increased rolling resistance and vice versa. Tread compositions typically contain one or more elastomers and one or more types of reinforcing materials such as particulate carbon black and silica; see, e.g., *The Vanderbilt Rubber Handbook,* 13th ed. (1990), pp. 603-04.

Filler(s), polymer(s), and additives typically are chosen so as to provide an acceptable compromise or balance of the desired properties. Ensuring that reinforcing filler(s) are well dispersed throughout the elastomeric material(s) both enhances processability and acts to improve physical properties. Dispersion of filler particles can be improved by increasing their interaction with the elastomer(s) and/or decreasing their interaction with each other. Examples of efforts of this type include high temperature mixing in the presence of selectively reactive promoters, surface oxidation of compounding materials, surface grafting, and chemically modifying the polymer, typically at a terminus thereof.

Terminal chemical modification often occurs by reaction of a living (i.e., anionically initiated) polymer with a functional terminating agent. Some of the numerous examples of this approach include U.S. Pat. Nos. 3,109,871, 4,647,625, 4,677,153, 5,109,907, 6,977,281, etc., as well as references cited therein and later publications citing these patents.

Terminal modification also can be provided by means of a functional initiator, in isolation or in combination with functional termination. Functional initiators typically are organolithium compounds that additionally include other functionality, typically functionality that includes a nitrogen atom, capable of interacting with one or more types of particulate filler materials.

Functional initiators generally have relatively poor solubility in hydrocarbon solvents of the type commonly used in anionic polymerizations. Further, many functional initiators also do not maintain propagation of living ends as well as more common alkyllithium initiators such as butyllithium. Both of these characteristics can negatively impact polymerization rate and efficiency.

At least some members of a new class of functional initiators described in WO 2009/086490 exhibit excellent solubility in hydrocarbon solvents, even aliphatic hydrocarbon solvents, and/or an ability to maintain propagation of living ends of polymer chains. Many of these compounds are most effective at only relatively moderate temperatures (e.g., below ~80° C.), however, meaning that their use typically is limited to systems or processes where heat transfer can be best accounted for, e.g., large reactor vessels, moderate polymerization rates (i.e., longer polymerizations), etc., which tend to be characteristic of batch processes.

SUMMARY

Provided herein is a group of compounds capable of anionically initiating polymerization of unsaturated monomers, even at the higher temperatures and shorter times involved in other than batch processes, e.g., semi-batch and continuous polymerizations.

In one aspect is provided a compound capable of anionically initiating polymerization of ethylenically unsaturated monomers. The compound can be represented by the formula

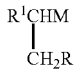

(I)

where M is an alkali metal atom, preferably Li, Na or K; $R^1$ is an aryl group that includes at least one $OR^2$ substituent group with $R^2$ being a group that is nonreactive toward M and capable of being hydrolyzed; and R is a hydrocarbyl group. Specific examples of compounds within the class defined by formula I particularly suitable for use as initiators for polymerization of ethylenically unsaturated monomers have the general formula

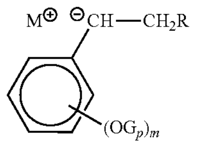

(Ia)

where M and R are defined as above, each $G_p$ independently is a protecting group, and m is an integer of from 1 to 5 inclusive. Advantageously, such compounds are soluble in the types of hydrocarbon solvents employed in anionic polymerizations and can be utilized at the relatively high temperatures experienced during continuous and semi-batch processes.

In another aspect is provided a method of making a functionalized polymer in a reaction vessel that involves initiating polymerization of one or more types of unsaturated monomers with a formula I or Ia compound. Portions of the initiating compound and/or the unsaturated monomers can be added after initiation of polymerization, i.e., the process can be other than batch. Further, the polymerization can be conducted at temperatures in excess of ~70° C., even up to ~120° C.

In a still further aspect is provided a process for providing an ionic compound capable of initiating polymerization of ethylenically unsaturated monomers. The process involves reacting a hydrocarbyl alkali metal compound with a styrenic compound having the general formula $$R^1CH{=}CH_2 \qquad \text{(II)}$$

where $R^1$ is defined as above in connection with formula I. Specific examples of compounds within the class defined by formula II include those having the general formula (IIa)

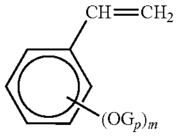

where $G_p$ and m are defined as above in connection with formula Ia. Formula II- and IIa-type compounds can be prepared by carbonyl methylenation of the corresponding aldehyde.

In some or all of the foregoing aspects, the polymer can include polyene mer units and, optionally, vinyl aromatic mer. In certain embodiments, the polyene can be one or more types of conjugated diene. In these and other embodiments, the polymer can be substantially random (i.e., the constituent monomers incorporate substantially randomly along the chain) and/or can be substantially linear. Also contemplated are block interpolymers, branched polymers, star-shaped polymers and the like.

The polymer can interact with particulate filler such as, e.g., carbon black. Compositions, including vulcanizates, that include particulate fillers and such polymers also are provided, as are methods of providing and using such compositions.

Other aspects of the present invention will be apparent to the ordinarily skilled artisan from the description that follows. To assist in understanding that description, certain definitions are provided immediately below, and these are intended to apply throughout unless the surrounding text explicitly indicates a contrary intention:

"polymer" means the polymerization product of one or more monomers and is inclusive of homo-, co-, ter-, tetra-polymers, etc.;

"mer" or "mer unit" means that portion of a polymer derived from a single reactant molecule (e.g., ethylene mer has the general formula —$CH_2CH_2$—);

"copolymer" means a polymer that includes mer units derived from two reactants, typically monomers, and is inclusive of random, block, segmented, graft, etc., copolymers;

"interpolymer" means a polymer that includes mer units derived from at least two reactants, typically monomers, and is inclusive of copolymers, terpolymers, tetra-polymers, and the like;

"substituted" means one containing a heteroatom or functionality (e.g., hydrocarbyl group) that does not interfere with the intended purpose of the group in question;

"directly bonded" means covalently attached with no intervening atoms or groups;

"polyene" means a molecule with at least two double bonds located in the longest portion or chain thereof, and specifically is inclusive of dienes, trienes, and the like;

"polydiene" means a polymer that includes mer units from one or more dienes;

"phr" means parts by weight (pbw) per 100 pbw rubber;

"radical" means the portion of a molecule that remains after reacting with another molecule, regardless of whether any atoms are gained or lost as a result of the reaction;

"aryl group" means a phenyl group or a polycyclic aromatic radical;

"gum Mooney viscosity" is the Mooney viscosity of an uncured polymer prior to addition of any filler(s);

"compound Mooney viscosity" is the Mooney viscosity of a composition that includes, inter alia, an uncured or partially cured polymer and particulate filler(s);

"terminus" means an end of a polymeric chain; and

"terminal moiety" means a group or functionality located at a terminus.

Throughout this document, all values given in the form of percentages are weight percentages unless the surrounding text explicitly indicates a contrary intention.

DETAILED DESCRIPTION

As apparent from the foregoing summary description, compounds defined by generally by formula I, including those defined by the more specific formula Ia, can be used to anionically initiate polymerization of one or more types of unsaturated monomers. Particularly where the resulting polymer is intended for use in a tire component, the polymer can include polyene mer units, particularly conjugated diene mer, and optionally vinyl aromatic mer units.

The polymer can be elastomeric and can include mer that include unsaturation such as those derived from polyenes, particularly dienes and trienes (e.g., myrcene). Illustrative polyenes include $C_4$-$C_{12}$ dienes, particularly conjugated dienes such as, but not limited to, 1,3-butadiene, isoprene, 1,3-pentadiene, 2,3-dimethyl-1,3-butadiene, and 1,3-hexadiene.

Polyenes can incorporate into polymeric chains in more than one way. Particularly for tire tread applications, controlling this manner of incorporation can be desirable; techniques for achieving this control are discussed below. A polymer chain with an overall 1,2-microstructure, given as a numerical percentage based on total polyene content, of from ~8 to ~80%, optionally from ~25 to ~65%, can be desirable for certain end use applications. A polymer that has an overall 1,2-microstructure of no more than ~50%, preferably no more than ~45%, more preferably no more than ~40%, even more preferably no more than ~35%, and most preferably no more than ~30%, based on total polyene content, is considered to be "substantially linear".

Directly bonded pendent aromatic groups can be provided through incorporation of mer units derived from vinyl aromatics, particularly the $C_8$-$C_{20}$ vinyl aromatics such as, e.g., styrene, α-methyl styrene, p-methyl styrene, the vinyl toluenes, and the vinyl naphthalenes. When used in conjunction with one or more polyenes in a random interpolymer (with mer units derived from each type of constituent monomer being incorporated in a non-repeating, essentially simultaneous manner), mer units with pendent aromaticity can constitute from ~1 to ~50%, from ~10 to ~45%, or from ~20 to ~40%, of the polymer chain. Random microstructure can provide particular benefit in some end use applications such as, e.g., rubber compositions used in the manufacture of tire treads. Where a block inter- or copolymer is desired, mer units with pendent aromaticity can constitute from ~1 to ~90%, generally from ~2 to ~80%, commonly from ~3 to ~75%, and typically ~5 to ~70% of the polymer chain.

Both randomization and vinyl content (i.e., 1,2-microstructure) of the polymer product can be increased by including a coordinator, usually a polar compound, in the polymerization ingredients; such a coordinator can be added separately, with one or more of the monomer(s), or with the initiator (if made outside of the polymerization vessel). Compounds useful as coordinators include organic compounds that include a heteroatom having a non-bonded pair of electrons (e.g., O or N), examples of which include dialkyl ethers of mono- and oligo-alkylene glycols; crown ethers; tertiary amines such as tetramethylethylene diamine; THF; THF oligomers; linear and cyclic oligomeric oxolanyl alkanes (see, e.g., U.S. Pat. No. 4,429,091) such as 2,2-bis(2'-tetrahydrofuryl)propane, di-piperidyl ethane, hexa-methylphosphoramide, N,N'-dimethylpiperazine, diazabicyclooctane, diethyl ether, tributylamine, and the like. Up to 90 or more equivalents of coordinator can be used per equivalent of initiator, depending on, for example, the amount of vinyl content desired, the level of non-polyene monomer employed, the reaction temperature, and nature of the specific coordinator employed.

Exemplary elastomers include interpolymers of one or more polyenes and styrene such as, e.g., poly(styrene-co-butadiene), also known as SBR.

The number average molecular weight ($M_n$) of the polymer typically is such that a quenched sample exhibits a gum Mooney viscosity ($ML_4$/100° C.) of from ~2 to ~150, more commonly from ~2.5 to ~125, even more commonly from ~5 to ~100, and most commonly from ~10 to ~75.

Both emulsion and solution polymerizations are commonly employed to make elastomers such as SBR, but the latter affords greater control with respect to such properties as randomness, microstructure, etc. Solution polymerizations have been performed since about the mid-20th century, so the general aspects thereof are known to the ordinarily skilled artisan; nevertheless, certain aspects are provided here for convenience of reference.

Both polar solvents, such as THF, and non-polar solvents can be employed in anionic polymerization techniques, with the latter type being more common in industrial practice. Examples of non-polar solvents include various $C_5$-$C_{12}$ cyclic and acyclic alkanes as well as their alkylated derivatives, certain liquid aromatic compounds, and mixtures thereof. The ordinarily skilled artisan is aware of other useful solvents and blends.

Most solution-type anionic polymerizations employ an alkyllithium initiator, such as n-butyllithium; a so-called multifunctional initiators which is capable of forming polymers with more than one living end; or a functionalized initiator of the type described in the Background section. Many of the functionalized initiators are poorly soluble in many of the solvents set forth above, particularly those that are relatively non-polar; conversely, many compounds defined by formula I exhibit acceptable solubility in the types of organic liquids commonly employed as solvents in solution polymerizations. Compounds included within this formula hereinafter are referred to as $R^1$-containing initiators. In such initiators, the countercation (M) is an alkali metal, preferably a K, Na or Li atom, most preferably a Li atom.

The aryl group of the $R^1$-containing initiator can be a phenyl group or two or more fused aromatic rings. Where the $R^1$ aryl group includes more than one $OR^2$ group (with each $R^2$ being a group that is nonreactive toward M), the $OR^2$ groups can be substituents of the same ring within the aryl group or can be substituents of different rings within the aryl group; where the aryl group contains three or more $OR^2$ groups, two of them can be substituents of one ring with the other(s) being substituent(s) of other ring(s). In one embodiment, two $OR^2$ groups can be at the 3 and 4 positions of the same ring within the aryl group, preferably a phenyl group. Where $R^1$ is other than a phenyl group and includes more than one $OR^2$ group and where the $OR^2$ groups are on more than one ring, at least two of the $OR^2$ groups preferably are at least somewhat proximate, i.e., directly bonded to ring C atoms that are separated by no more than 4, preferably 3, and even more preferably 2, other ring atoms. Where a single $OR^2$ group is present on a phenyl group, it can be located at any ring position, although para from the vinyl group might be preferable for certain applications.

The $R^2$ moieties of the $R^1$-containing initiator, which need not be identical although ease and simplicity typically result in a single type of $R^2$ for a given $R^1$-containing initiator, ensure that the $R^1$-containing initiator contains no active hydrogen atoms, which would interfere with the ability of the $R^1$-containing initiator to anionically initiate polymerizations. Unless a particular $R^2$ constitutes a moiety that is capable of providing interactivity with particulate filler (some of which are used in the following examples), it preferably also is capable of being hydrolyzed so as to provide phenolic hydroxyl groups after the $R^1$-containing initiator is utilized in a polymerization, during which it forms one end of the polymer chain. This type of terminal unit has been found to provide excellent interactivity with a wide variety of particulate fillers including carbon black and silica as well as non-conventional fillers such as inorganic oxides and hydroxides, clays and the like.

Compounds defined by formula I can be provided by reacting a styrenic compound defined by general formula II with a hydrocarbyl alkali metal compound of the general formula $R^3M$ where $R^3$ is an alkyl (typically $C_2$-$C_{10}$ alkyl), cycloalkyl (typically $C_2$-$C_{10}$ cycloalkyl) or aryl group. Exemplary $R^3M$ compounds include, but are not limited to, n-butyllithium, phenyllithium, sec-butyllithium, tert-butyllithium, alkali metal naphthalates, etc.

Formula II-type compounds can be provided from by carbonyl methylenation of appropriate aldehydes. For example, the set of species defined by formula IIa, where the aryl group is a phenyl group, can be provided from a compound of the general formula

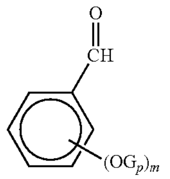

(III)

where $G_p$ and m are defined as above, using a Wittig reagent, Tebbe reagent, or the like. A specific Wittig-type methylenation reaction is provided below in the examples that follow.

The $R^1$-containing initiator can be made external to the polymerization vessel where it is to act as an initiator; in this case, a blend of monomer(s) and solvent can be charged to the reaction vessel, followed by addition of initiator, which often is added as part of a solution or blend (i.e., in a solvent carrier). Alternatively, the $R^1$-containing initiator can be synthesized in situ.

In a batch process, a solution of polymerization solvent(s) and the monomer(s) is provided at a temperature of from about −80° to ~100° C., more commonly from about −40° to ~50° C., and typically from ~0° to ~30° C.; to this solution, the $R^1$-containing initiator (or a precursor and a hydrocarbyllithium, typically an alkyllithium) is added. The solution can have a temperature of from about −70° to ~150° C., more commonly from about −20° to ~120° C., and typically from ~10° to ~100° C. The polymerization is allowed to proceed for a period of time sufficient to result in the formation of the desired polymer, usually from ~0.01 to ~100 hours, more commonly from ~0.08 to ~48 hours, and typically from ~0.15 to ~2 hours. Anionic polymerizations typically are carried out under anhydrous, anaerobic conditions, commonly with agitation.

For a semi-batch process, the foregoing batch description is modified by metering, discontinuously or continuously, into the reaction vessel one or more of the ethylenically unsaturated monomers and/or the polar modifier(s). While the temperature ranges at which semi-batch processes typically are run are similar to those of batch processes, the lesser amounts of monomer being converted at any given time simplify heat transfer considerations and, accordingly, often are run at the higher ends of the various ranges. Additionally, metering of one or more of the types of monomers and/or polar modifiers can permit greater control of polymer microstructure. An exemplary semi-batch process is provided below in the examples.

For a continuous process, the batch process is modified by discontinuously or continuously metering into the reaction vessel all reactants and additives, i.e., the ethylenically unsaturated monomers, coordinator(s), $R^1$-containing initiator, and the like. The temperature ranges at which continuous processes typically are run tend to be similar to those of batch processes. Continuous processes typically are considered to be more efficient (production output) than batch or semi-batch processes. An exemplary continuous process is provided below in the examples. For additional information on such processes, see U.S. Pat. Nos. 7,442,748, 6,897,270, and 5,489,660, as well as patents and publications cited by and citing these patents.

After a desired degree of conversion has been reached, the heat source (if used) can be removed and, if the reaction vessel is to be reserved solely for polymerizations, the reaction mixture is removed to a post-polymerization vessel for functionalization and/or quenching. At this point, the reaction mixture commonly is referred to as a "polymer cement" because of its relatively high concentration of polymer. Further, each living polymer chain has a directly bonded $R^1$-containing initiator radical, which means that those polymer chains are deemed to be functionalized.

The polymer is considered to include terminal functionality from the $R^1$-containing initiator. However, where additional or other functionality is desired to enhance interaction with particulate filler, the polymer can be further functionalized by reaction with an appropriate terminating reagent, coupling agent and/or linking agent. The ordinarily skilled artisan is familiar with numerous examples of terminal functionalities that can be provided through this type of post-polymerization functionalization. For additional details, the interested reader is directed to any of U.S. Pat. Nos. 4,015,061, 4,616,069, 4,935,471, 5,153,159, 5,149,457, 5,196,138, 5,329,005, 5,496,940, 5,502,131, 5,567,815, 5,610,227, 5,663,398, 5,786,441, 6,812,295, 7,153,919, etc., as well as references cited in these patents and later publications citing these patents; see also U.S. Patent Publ. Nos. 2007/0149744, 2007/0037956, 2007/0078232, 2008/0027171, and the like. Specific exemplary functionalizing compounds include $SnCl_4$, $R^2_3SnCl$, $R^2_2SnCl_2$, $R^2SnCl_3$, carbodiimides, N-cyclic amides, N,N'-disubstituted cyclic ureas, cyclic amides, cyclic ureas, isocyanates, Schiff bases, 4,4'-bis(diethylamino)benzophenone, alkyl thiothiazolines, alkoxysilanes (e.g., $Si(OR^2)_4$, $R^2Si(OR^2)_3$, $R^2_2Si(OR^2)_2$, etc.) cyclic siloxanes and mixtures thereof (In the foregoing, each $R^2$ independently is a $C_1$-$C_{20}$ alkyl group, $C_3$-$C_{20}$ cycloalkyl group, $C_6$-$C_{20}$ aryl group, or $C_7$-$C_{20}$ aralkyl group.) Specific examples of preferred functionalizing compounds include $SnCl_4$, tributyl tin chloride, dibutyl tin dichloride, and 1,3-dimethyl-2-imidazolidinone (DMI).

Reaction of most types of functionalizing compounds with living polymers can be performed relatively quickly (a few minutes to a few hours) at moderate temperatures (e.g., 0° to 75° C.). Although not always necessary, quenching can be conducted by stirring the polymer and an active hydrogen-containing compound, such as an alcohol or acid, for up to ~120 minutes at temperatures of from ~25° to ~150° C.

During polymerization and any optional post-polymerization functionalization, most of the $R^2$ groups probably remain in the hydrolyzable group category; in other words, the anhydrous, anaerobic conditions typically present in the polymerization vessel are such that essentially all $R^2$ moieties from the $R^1$-containing initiator remain. Ensuring that most, if not all, of the $R^2$ groups are converted to hydrogen atoms often is desirable to enhance interactivity between the functionalized polymer and particulate filler (when the polymer is used in filled compositions). While functionalizing reaction conditions (or the conditions involved in quenching and processing, described below) might be sufficient to hydrolyze some of the $R^2$ groups, a separate hydrolysis reaction designed to ensure complete conversion to H atoms can be utilized. The ordinarily skilled artisan is aware of a variety of potentially useful hydrolyzing reactions, although one exemplary route is set forth in the examples.

Solvent can be removed from the quenched polymer cement by conventional techniques such as drum drying, extruder drying, vacuum drying or the like, which may be combined with coagulation with water, alcohol or steam, thermal desolvation, etc.; if coagulation is performed, oven drying may be desirable.

The resulting polymer can be utilized in a tread stock compound or can be blended with any conventionally employed tread stock rubber including natural rubber and/or non-functionalized synthetic rubbers such as, e.g., one or more of homo- and interpolymers that include just polyene-derived mer units (e.g., poly(butadiene), poly(isoprene), and copolymers incorporating butadiene, isoprene, and the like), SBR, butyl rubber, neoprene, EPR, EPDM, acrylonitrile/butadiene rubber (NBR), silicone rubber, fluoroelastomers, ethylene/acrylic rubber, EVA, epichlorohydrin rubbers, chlorinated polyethylene rubbers, chlorosulfonated polyethylene rubbers, hydrogenated nitrile rubber, tetrafluoroethylene/propylene rubber and the like. When a functionalized polymer(s) is blended with conventional rubber(s), the amounts can vary from about 5 to about 99% of the total rubber, with the conventional rubber(s) making up the balance of the total rubber. The minimum amount depends to a significant extent on the degree of hysteresis reduction desired.

Amorphous silica ($SiO_2$) can be utilized as a filler. Silicas are generally classified as wet-process, hydrated silicas because they are produced by a chemical reaction in water, from which they are precipitated as ultrafine, spherical particles. These primary particles strongly associate into aggregates, which in turn combine less strongly into agglomerates. "Highly dispersible silica" is any silica having a very substantial ability to de-agglomerate and to disperse in an elastomeric matrix, which can be observed by thin section microscopy.

Surface area gives a reliable measure of the reinforcing character of different silicas; the Brunauer, Emmet and Teller ("BET") method (described in *J. Am. Chem. Soc.*, vol. 60, p. 309 et seq.) is a recognized method for determining surface area. BET surface area of silicas generally is less than 450 $m^2/g$, and useful ranges of surface include from ~32 to ~400 $m^2/g$, ~100 to ~250 $m^2/g$, and ~150 to ~220 $m^2/g$.

The pH of the silica filler is generally from ~5 to ~7 or slightly over, preferably from ~5.5 to ~6.8.

Some commercially available silicas which may be used include Hi-Sil™ 215, Hi-Sil™ 233, and Hi-Sil™ 190 (PPG Industries, Inc.; Pittsburgh, Pa.). Other suppliers of commercially available silica include Grace Davison (Baltimore, Md.), Degussa Corp. (Parsippany, N.J.), Rhodia Silica Systems (Cranbury, N.J.), and J.M. Huber Corp. (Edison, N.J.).

Silica can be employed in the amount of ~1 to ~100 phr, preferably in an amount from ~5 to ~80 phr. The useful upper range is limited by the high viscosity that such fillers can impart.

Other useful fillers include all forms of carbon black including, but not limited to, furnace black, channel blacks and lamp blacks. More specifically, examples of the carbon blacks include super abrasion furnace blacks, high abrasion furnace blacks, fast extrusion furnace blacks, fine furnace blacks, intermediate super abrasion furnace blacks, semi-reinforcing furnace blacks, medium processing channel blacks, hard processing channel blacks, conducting channel blacks, and acetylene blacks; mixtures of two or more of these can be used. Carbon blacks having a surface area (EMSA) of at least 20 $m^2/g$, preferably at least ~35 $m^2/g$, are preferred; surface area values can be determined by ASTM D-1765 using the CTAB technique. The carbon blacks may be in pelletized form or an unpelletized flocculent mass, although unpelletized carbon black can be preferred for use in certain mixers.

The amount of carbon black can be up to ~50 phr, with ~5 to ~40 phr being typical. When carbon black is used with silica, the amount of silica can be decreased to as low as ~1 phr; as the amount of silica decreases, lesser amounts of the processing aids, plus silane if any, can be employed.

Elastomeric compounds typically are filled to a volume fraction, which is the total volume of filler(s) added divided by the total volume of the elastomeric stock, of ~25%; accordingly, typical (combined) amounts of reinforcing fillers, i.e., silica and carbon black, is ~30 to 100 phr.

When silica is employed as a reinforcing filler, addition of a coupling agent such as a silane is customary so as to ensure good mixing in, and interaction with, the elastomer(s). Generally, the amount of silane that is added ranges between ~4 and 20%, based on the weight of silica filler present in the elastomeric compound.

Coupling agents can have a general formula of A-T-Q, in which A represents a functional group capable of bonding physically and/or chemically with a group on the surface of the silica filler (e.g., surface silanol groups); T represents a hydrocarbon group linkage; and Q represents a functional group capable of bonding with the elastomer (e.g., via a sulfur-containing linkage). Such coupling agents include organosilanes, in particular polysulfurized alkoxysilanes (see, e.g., U.S. Pat. Nos. 3,873,489, 3,978,103, 3,997,581, 4,002,594, 5,580,919, 5,583,245, 5,663,396, 5,684,171, 5,684,172, 5,696,197, etc.) or polyorganosiloxanes bearing the Q and A functionalities mentioned above. An exemplary coupling agent is bis[3-(triethoxysilyl)propyl]tetrasulfide.

Addition of a processing aid can be used to reduce the amount of silane employed. See, e.g., U.S. Pat. No. 6,525,118 for a description of fatty acid esters of sugars used as processing aids. Additional fillers useful as processing aids include, but are not limited to, mineral fillers, such as clay (hydrous aluminum silicate), talc (hydrous magnesium silicate), and mica as well as non-mineral fillers such as urea and sodium sulfate. The additional fillers can be utilized in an amount of up to about 40 phr, typically up to ~20 phr.

Other conventional rubber additives also can be added. These include, for example, process oils, plasticizers, anti-degradants such as antioxidants and antiozonants, curing agents and the like.

All of the ingredients can be mixed using standard equipment such as, e.g., Banbury or Brabender mixers. Typically, mixing occurs in two or more stages. During the first stage (often referred to as the masterbatch stage), mixing typically is begun at temperatures of ~120° to ~130° C. and increases until a so-called drop temperature, typically ~165° C., is reached.

Where a formulation includes silica, a separate re-mill stage often is employed for separate addition of the silane component(s). This stage often is performed at temperatures similar to, although often slightly lower than, those employed in the masterbatch stage, i.e., ramping from ~90° C. to a drop temperature of ~150° C.

Reinforced rubber compounds conventionally are cured with about 0.2 to about 5 phr of one or more known vulcanizing agents such as, for example, sulfur or peroxide-based curing systems. For a general disclosure of suitable vulcanizing agents, the interested reader is directed to an overview such as that provided in Kirk-Othmer, *Encyclopedia of Chem. Tech.*, 3d ed., (Wiley Interscience, New York, 1982), vol. 20, pp. 365-468. Vulcanizing agents, accelerators, etc., are added at a final mixing stage. To ensure that onset of vulcanization does not occur prematurely, this mixing step often is done at lower temperatures, e.g., starting at ~60° to ~65° C. and not going higher than ~105° to ~110° C.

The following non-limiting, illustrative examples are intended to provide exemplary conditions and materials that can be useful in the practice of the present invention.

EXAMPLES

Butadiene solution (22.5% in hexane), styrene solution (33.5% in hexane), hexane, n-butyllithium (1.70 M in hexane), 2,2-bis(2'-tetrahydrofuryl)propane (1.6 M solution in hexane, stored over $CaH_2$), butylated hydroxytoluene (BHT) solution in hexane, and 3-bis(trimethylsilyl)aminopropylmethyldiethoxysilane (1.0 M in hexane) were used in these examples.

Commercially available reagents and starting materials included the following, all of which were used without further purification unless otherwise noted in a specific example:

- from Sigma-Aldrich Co.—3,4-dihydroxybenzaldehyde (97%), 4-hydroxybenzaldehyde (98%), 2,3-dihydroxybenzaldehyde (97%), 3,5-dihydroxybenzaldehyde (98%), 2,5-dihydroxybenzaldehyde (98%), 3,4,5-trihydroxybenzaldehyde monohydrate (98%), methyltriphenylphosphonium bromide (MTP-Br, 98%), p-toluenesulfonic acid monohydrate (98.5%), ethyl acetate (99.5%), and 4-di(methylamino)pyridine (DMAP, 99%), and
- from ACROS Organics—tert-butyldimethylsilyl chloride (98%) and tetrabutylammonium fluoride (TBAF, 1 M in THF, containing ~5% water).

Testing data in the Examples was performed on filled compositions made according to the formulations shown in Tables 1a (a formulation employing only carbon black as a particulate filler) and 1b (a formulation employing only silica as a particulate filler). In these tables, N-phenyl-N'(1,3-dimethylbutyl)-p-phenyldiamine acts as an anti-oxidant while 2,2'-dithiobisbenzothiazole, N-t-butylbenzothiazole-2-sulfenamide, and N,N'-diphenylguanidine act as accelerators.

TABLE 1a

| Composition for vulcanizates, carbon black filler | |
|---|---|
| | Amount (phr) |
| Masterbatch | |
| polymer | 100 |
| carbon black (N343 type) | 50 |
| wax | 2 |
| N-phenyl-N'-(1,3-dimethylbutyl)-p-phenylenediamine | 0.95 |
| stearic acid | 2 |
| processing oil (low PCA content) | 10 |
| Final | |
| sulfur | 1.5 |
| N-cyclohexylbenzothiazole-2-sulfenamide | 0.5 |
| N,N'-diphenylguanidine | 0.3 |
| 2,2'-dithiobisbenzothiazole | 0.5 |
| ZnO | 2.5 |
| TOTAL | 170.25 |

TABLE 1b

| Composition for vulcanizates, silica filler | |
|---|---|
| | Amount (phr) |
| Masterbatch | |
| synthesized polymer | 80 |
| poly(isoprene) (natural rubber) | 20 |
| silica | 52.5 |
| wax | 2 |
| N-phenyl-N'-(1,3-dimethylbutyl)-p-phenyldiamine | 0.95 |
| stearic acid | 2 |
| processing oil (low PCA content) | 10 |
| Re-mill | |
| silica | 2.5 |
| silane | 5 |
| Final | |
| sulfur | 1.5 |
| ZnO | 2.5 |
| 2,2'-dithiobisbenzothiazole | 2.0 |
| N-t-butylbenzothiazole-2-sulfenamide | 0.7 |
| N,N'-diphenylguanidine | 1.4 |
| TOTAL | 183.05 |

Data corresponding to "Dynastat tan δ" were acquired from tests conducted on a Dynastat™ mechanical spectrometer (Dynastatics Instruments Corp.; Albany, N.Y.) using the following conditions: 1 Hz, 2 kg static mass and 1.25 kg dynamic load, a cylindrical (9.5 mm diameter×16 mm height) vulcanized rubber sample, and 60° C.

Data corresponding to "Bound rubber" were determined using the procedure described by J. J. Brennan et al., *Rubber Chem. and Tech.,* 40, 817 (1967).

Mooney viscosity ($ML_{1+4}$) values were determined with an Alpha Technologies™ Mooney viscometer (large rotor) using a one-minute warm-up time and a four-minute running time; tensile mechanical properties were determined using the standard procedure described in ASTM-D412; Payne effect (ΔG', i.e., the difference between G' at 0.25% strain and at 14% strain) and hysteresis (tan δ) data were obtained from dynamic experiments conducted at 60° C. and 10 Hz (strain sweep) and 2% strain and 10 Hz (temperature sweep). With respect to tensile properties, $M_X$ is modulus at X % elongation, $T_b$ is tensile strength at break, and $E_b$ is percent elongation at break.

Example 1

3,4-di(tert-butyldimethylsiloxyl)benzaldehyde

To a dry flask fitted with a magnetic stirring bar was introduced ~8.3 g 3,4-dihydroxybenzaldehyde, ~0.5 g DMAP, 30 mL triethylamine, and 100 mL THF. A solution of ~19.0 g tert-butyldimethylsilyl chloride in 50 mL THF was added slowly via syringe. The reaction mixture was stirred for ~1 hour at room temperature. Solid was filtered and the filtrate evaporated. The residue was purified by silica gel column chromatography (200-425 mesh from Fisher Scientific) with hexane/ethyl acetate (90:10, v/v) as eluent. Approximately 21.3 g (96.8% yield) of a colorless oily, waxy product was obtained. Proton and $^{13}C$ NMR spectroscopic analysis confirmed the product as 3,4-bis(tert-butyldimethylsiloxyl)benzaldehyde [3,4-(TBDMSO)BA].

Examples 2-5

Synthesis of Functional Styrenes

To a stirred 0° C. solution of 23.2 g MTP-Br in 100 mL dried THF under nitrogen was dropwise added 40.6 mL n-BuLi solution. After ~15 minutes, a solution of ~22.3 g 3,4-(TBDMSO)BA (from Example 1) in 30 mL THF was dropwise added via syringe. The resulting yellow suspension was stirred for ~4 hours before being treated with $NH_4Cl$. This solution was filtered and concentrated under vacuum. The residue was purified by silica gel column chromatography with hexane/ethyl acetate (95:5, v/v) as eluent, resulting in collection of ~20.6 g (94% yield) of a colorless oil. Proton and $^{13}C$ NMR confirmed the compound to be 3,4-di(tert-butyldimethylsiloxyl)styrene [3,4-TBDMSOS, Example 2].

Similar procedures were used to make 3,4,5-tri(tert-butyldimethylsiloxyl)-styrene [3,4,5-TBDMSOS, Example 3] (90%, colorless liquid) from 3,4,5-trihydroxybenzaldehyde monohydrate, 3,5-di(tert-butyldimethylsiloxyl)styrene [3,5-TBDMSOS, Example 4] (88%, colorless liquid) from 3,5-dihydroxybenzaldehyde, and 4-(tert-butyldimethylsiloxyl)-styrene [4-TBDMSOS, Example 5] (91%, colorless liquid) from 4-hydroxybenzaldehyde.

Examples 6-11

Semi-Batch Polymerizations Using Functionalized Styrene Monomers

In a purged, dried glass bottle at room temperature, 3.34 mL n-butyllithium solution followed by 1.10 mL 2,2-bis(2'-tetrahydrofuryl)propane solution was added to 5.7 mL of a 1.0 M solution of 3,4-TBDMSOS (from Example 2) in hexane. A deep red solution immediately formed and, after ~5 minutes, this was charged to a $N_2$-purged reactor equipped with a stirrer pre-heated to 82° C.

Metering from a blend tank equipped with a flow meter of a pre-mixed solution of 1.73 kg hexane, 0.66 kg styrene solution, and 2.04 kg butadiene solution was begun at a flow rate of ~0.45 g/sec over ~2 hour. After ~5 minutes of metering to the reactor, the batch temperature peaked at ~85° C.

After another ~15 minutes, the polymer cement was dropped into dried glass bottles and treated as follows:

- Ex. 6 terminated with isopropanol
- Ex. 7 terminated with isopropanol, agitation for ~30 minutes at 50° C., addition of TBAF solution (~6:5 molar ratio relative to initiator) to hydrolyze protecting groups, agitation at room temperature for ~1 hour Ex. 8 addition of 1.0 M 3,4-TBDMSOS (from Example 2) in hexane (~1:1 molar ratio relative to initiator), agitation for ~30 minutes at 50° C., addition of TBAF solution (~6:5 molar ratio relative to initiator) to hydrolyze protecting groups, agitation at room temperature for ~1 hour Ex. 9 addition of 1.0 M 3,4-(TBDMSO)BA (from Example 1) in hexane (~1:1 molar ratio relative to initiator), agitation for ~30 minutes at 50° C., addition of TBAF solution (~6:5 molar ratio relative to initiator) to hydrolyze protecting groups, agitation at room temperature for ~1 hour Ex. 10 addition of 3-bis(trimethylsilyl)aminopropyl-methyldiethoxysilane solution (~1:1 molar ratio relative to initiator), agitation for ~30 minutes at 50° C., addition of TBAF solution (~6:5 molar ratio relative to initiator) to hydrolyze protecting groups, agitation at room temperature for ~1 hour Ex. 11 addition of 0.25 M solution of $SnCl_4$ in hexane (~1:4 molar ratio relative to initiator), agitation for ~30 minutes at 50° C.

Each of the polymer cements were dropped into isopropanol containing BHT before being drum dried. The properties of these functionalized polymers are provided below in Table 2, where $M_p$ represents peak molecular weight and 1,2-microstructure percentages are based on total amount of butadiene employed.

TABLE 2

| | Polymer properties | | | | | |
|---|---|---|---|---|---|---|
| | 6 | 7 | 8 | 9 | 10 | 11 |
| $M_n$ (kg/mol) | 166 | 155 | 156 | 152 | 145 | 208 |
| $M_w/M_n$ | 1.12 | 1.20 | 1.24 | 1.32 | 1.24 | 1.73 |
| $M_p$ (kg/mol) | 192 | 191 | 191 | 192 | 191 | 190 |
| coupling (%) | 3.63 | 7.14 | 11.05 | 10.73 | 5.93 | 48.05 |

Examples 12-14

Continuous Polymerizations Using Functionalized Styrene Monomers

A ~25 L reactor with a 25 minute residence time was filled with hexane, and its jacket temperature was set to 90.5° C.

To the bottom of the reactor were metered ~1.98 g/sec styrene solution (31.8% by wt. in hexane), ~4.72 g/sec butadiene solution (21.7% by wt. in hexane), ~2.31 g/sec hexane, ~0.23 g/sec 2,2-bis(2'-tetrahydrofuryl)propane (0.027 M in hexane), ~0.0012 $cm^3$/sec 1,2-butadiene (13.8%), ~0.97 g/sec of a 0.08 M solution of 3,4-TBDMSOS in hexane, and ~0.97 g/sec n-butyllithium (0.08 M in hexane). At the midpoint of the reactor, an additional stream of ~1.17 g/sec butadiene solution was added to minimize block styrene formation.

Under these conditions, ~18% total solids polymer formed in the reactor. Polymer cement was removed at the top of the reactor into a storage vessel.

After 60-90 minutes of polymerization time, a steady state was achieved (top reactor temperature of 94.4° C., low temperature of 82.8° C.). After another ~60 minutes of polymerization, samples were taken at the top of the reactor and drum-dried. NMR testing showed ~36% styrene content and ~41% 1,2-microstructure; the polymer exhibited a Mooney ($ML_{1+4}$) viscosity of 49.7 and a $t_{80}$ of 3.2 sec. Polymer cement was collected in a storage tank and terminated with isopropanol; the polymer exhibited a final Mooney ($ML_{1+4}$) viscosity of 56.4 and a $t_{80}$ of 3.1 sec. This is designated Example 12 below.

Two additional polymerizations were conducted, using similar techniques, to provide polymer cement concentrations of 16% and 20%. These are designated Examples 13 and 14, respectively, below.

The properties of the polymers of Examples 12-14 are summarized in the following table. Styrene content and 1,2-microstructure were determined by NMR.

TABLE 3

| | Polymer properties | | |
|---|---|---|---|
| | 12 | 13 | 14 |
| $M_n$ (kg/mol) | 117 | 112 | 103 |
| $M_w/M_n$ | 2.46 | 2.06 | 2.56 |
| $T_g$ (° C.) | −33.7 | −31.1 | −34.6 |
| $ML_{1+4}$ @ 100° C. | 50 | 45 | 55 |
| $t_{80}$ (sec) | 3.2 | 2.4 | 5.0 |
| Total styrene (%) | 36.2 | 35.9 | 36.3 |
| 1,2-microstructure (%) | 40.9 | 43.8 | 41.8 |

Examples 15-21

Comparison of Initiators

Batch polymerizations were conducted so as to provide three styrene/butadiene interpolymers. One polymerization employed n-butyllithium as initiator (using a procedure similar to those employed in the examples section of WO 2009/086490), a second employed hexamethyleneimine (HMI) as initiator (see U.S. Pat. No. 5,329,005), and a third employed 3,4-TBDMSOS (see Example 2) as initiator.

Portions of each polymer cement was dropped into dried glass bottles and treated as follows:

Initiated with n-Butyllithium

Ex. 15: terminated with isopropanol

Initiated with HMI

Ex. 16: terminated with isopropanol

Ex. 17: addition of 3,4-(TBDMSO)BA (from Ex. 1) (~1:1 molar ratio relative to initiator), agitation for ~30 minutes at 50° C., addition of TBAF solution to hydrolyze protecting groups, agitation at room temperature for ~1 hour Ex. 18: addition of $SnCl_4$ in hexane (~1:4 molar ratio relative to initiator), agitation Initiated with 3,4-TBDMSOS Ex. 19: terminated with isopropanol, followed by addition of TBAF solution to hydrolyze protecting groups, agitation at room temperature for ~1 hour Ex. 20: addition of 3,4-(TBDMSO)BA (from Ex. 1) (~1:1 molar ratio relative to initiator), agitation for ~30 minutes at 50° C., addition of TBAF solution to hydrolyze protecting groups, agitation at room temperature for ~1 hour Ex. 21: addition of $SnCl_4$ in hexane (~1:4 molar ratio relative to initiator), agitation Each of these polymer cements was dropped into isopropanol containing BHT before being drum dried. The properties of these functionalized polymers are provided below in Table 4.

TABLE 4

| Polymer properties | | | | | | | |
|---|---|---|---|---|---|---|---|
| | 15 | 16 | 17 | 18 | 19 | 20 | 21 |
| $M_n$ (kg/mol) | 128 | 108 | 113 | 201 | 133 | 144 | 224 |
| $M_w/M_n$ | 1.03 | 1.05 | 1.10 | 1.43 | 1.07 | 1.19 | 1.39 |
| $M_p$ (kg/mol) | 133 | 114 | 114 | 374 | 136 | 136 | 439 |
| $T_g$ (° C.) | −37.7 | −36.8 | −36.3 | −36.6 | −36.7 | −37.2 | −36.7 |
| coupling (%) | 0.6 | 1.0 | 7.7 | 72.1 | 6.4 | 20.3 | 64.2 |

Examples 22-35

Preparation and Testing of Vulcanizates

Using the formulations from Tables 1a and 1b above, rubber compounds containing reinforcing fillers were prepared from the polymers of Examples 15-21. These compounds were cured for 15 minutes at 171° C. to provide vulcanizates 22-28 (carbon black) and 29-35 (silica), respectively.

Results of physical testing on vulcanizates made from these polymers are summarized below in Tables 5 and 6; for the "Temp. sweep" line, the top row of data are from measurements at 0° C. while the bottom row are from measurements at 60° C. Strain sweep test results are tabulated in Tables 7 and 8.

The data from these tables show that SBR interpolymers made using functional initiators exhibit excellent interaction with carbon black and, in particular, silica filler as evidenced by decrease in high temperature tan δ, reduction in ΔG', increased low temperature tan δ, and the like.

TABLE 5

| Compound and vulcanizate properties, Examples 22-28 (carbon black) | | | | | | | |
|---|---|---|---|---|---|---|---|
| | 22 | 23 | 24 | 25 | 26 | 27 | 28 |
| synthetic polymer (example no.) | 15 | 16 | 17 | 18 | 19 | 20 | 21 |
| Bound rubber (%) | 11.1 | 33.6 | 43.9 | 49.3 | 16.9 | 42.8 | 30.6 |
| MDR2000 @ 171° C. (final) | | | | | | | |
| ML (kg · cm) | 0.90 | 1.08 | 2.12 | 2.37 | 1.16 | 2.15 | 1.64 |
| MH (kg · cm) | 17.85 | 17.57 | 19.31 | 17.65 | 18.85 | 18.17 | 16.94 |
| $t_{90}$ (min) | 6.29 | 7.10 | 9.58 | 6.79 | 8.70 | 9.70 | 6.87 |
| Compound $ML_{1+4}$ @ 130° C. (final) | 23.5 | 30.5 | 65.0 | 62.2 | 34.7 | 69.1 | 47.2 |
| Dynatstat ™ tan δ @ 60° C. (final) | 0.2165 | 0.1230 | 0.0854 | 0.0931 | 0.1707 | 0.0973 | 0.1233 |
| Tensile @ 23° C. (final, unaged) | | | | | | | |
| $M_{50}$ (MPa) | 1.33 | 1.23 | 1.31 | 1.12 | 1.35 | 1.23 | 1.18 |
| $M_{300}$ (MPa) | 6.08 | 8.42 | 10.12 | 9.77 | 7.01 | 7.28 | 6.84 |
| $T_b$ (MPa) | 17.9 | 20.7 | 20.4 | 20.5 | 17.4 | 20.9 | 17.2 |
| $E_b$ (%) | 756 | 610 | 518 | 517 | 638 | 669 | 594 |
| Tensile @ 100° C. (final, unaged) | | | | | | | |
| $M_{50}$ (MPa) | 1.00 | 1.00 | 1.19 | 0.95 | 1.08 | 1.08 | 0.95 |
| $M_{300}$ (MPa) | 5.22 | 7.39 | 8.79 | 8.39 | 5.98 | 5.13 | 5.92 |
| $T_b$ (MPa) | 8.1 | 8.7 | 9.9 | 9.9 | 9.0 | 7.0 | 9.1 |
| $E_b$ (%) | 440 | 338 | 328 | 338 | 424 | 323 | 414 |
| Strain sweep (60° C., 10 Hz, final) | | | | | | | |
| G' @ 5% strain (MPa) | 3.027 | 2.184 | 2.222 | 2.102 | 2.808 | 2.359 | 2.193 |
| G" @ 5% strain (MPa) | 0.689 | 0.321 | 0.204 | 0.202 | 0.516 | 0.235 | 0.276 |
| tan δ @ 5% strain | 0.2277 | 0.1468 | 0.0920 | 0.0960 | 0.1837 | 0.0997 | 0.1260 |
| ΔG' (MPa) | 4.217 | 1.069 | 0.579 | 0.538 | 2.519 | 0.755 | 0.826 |
| Temp. sweep (2% strain, 10 Hz, final) | | | | | | | |
| G' (MPa) | 13.482 | 11.511 | 9.074 | 8.247 | 13.062 | 8.701 | 9.080 |
| | 5.051 | 4.158 | 3.849 | 3.408 | 4.866 | 3.661 | 3.445 |
| G" (MPa) | 4.884 | 4.874 | 3.829 | 3.549 | 5.436 | 3.710 | 4.024 |
| | 1.170 | 0.749 | 0.458 | 0.390 | 0.925 | 0.445 | 0.516 |
| tan δ | 0.3618 | 0.4224 | 0.4208 | 0.4295 | 0.4154 | 0.4255 | 0.4418 |
| | 0.2315 | 0.1801 | 0.1190 | 0.1143 | 0.1901 | 0.1215 | 0.1498 |

TABLE 6

| Compound and vulcanizate properties, Examples 29-35 (silica) | | | | | | | |
|---|---|---|---|---|---|---|---|
| | 29 | 30 | 31 | 32 | 33 | 34 | 35 |
| synthetic polymer (example no.) | 15 | 16 | 17 | 18 | 19 | 20 | 21 |
| Bound rubber (%) | 24.3 | 21.5 | 37.2 | 33.6 | 35.2 | 50.2 | 35.6 |
| MDR2000 @ 171° C. (final) | | | | | | | |
| ML (kg · cm) | 1.83 | 1.78 | 1.83 | 3.50 | 1.82 | 2.24 | 3.37 |
| MH (kg · cm) | 24.84 | 26.01 | 23.53 | 27.08 | 23.89 | 21.81 | 25.09 |
| $t_{90}$ (min) | 6.73 | 7.75 | 6.51 | 6.75 | 6.09 | 4.55 | 6.40 |
| Compound $ML_{1+4}$ @ 130° C. (final) | 20.3 | 15.9 | 35.9 | 43.1 | 27.2 | 66.8 | 47.3 |
| Dynatstat ™ tan δ @ 60° C. (final) | 0.1327 | 0.1125 | 0.0684 | 0.0933 | 0.1146 | 0.0614 | 0.1065 |
| Tensile @ 23° C. (final, unaged) | | | | | | | |
| $M_{50}$ (MPa) | 1.91 | 2.00 | 1.91 | 2.19 | 1.89 | 1.75 | 2.00 |
| $M_{300}$ (MPa) | 10.43 | 11.49 | 13.86 | 12.64 | 11.24 | 12.63 | 11.15 |
| $T_b$ (MPa) | 15.0 | 13.1 | 15.4 | 14.5 | 15.0 | 15.3 | 14.3 |
| $E_b$ (%) | 406 | 333 | 327 | 334 | 381 | 349 | 371 |
| Tensile @ 100° C. (final, unaged) | | | | | | | |
| $M_{50}$ (MPa) | 1.68 | 1.78 | 1.95 | 1.99 | 1.74 | 1.74 | 1.88 |
| $M_{200}$ (MPa) | 5.85 | 6.30 | 7.80 | 7.02 | 6.36 | 6.96 | 6.53 |
| $T_b$ (MPa) | 7.2 | 8.4 | 8.1 | 8.8 | 7.7 | 7.4 | 6.9 |
| $E_b$ (%) | 243 | 257 | 207 | 246 | 239 | 209 | 213 |
| Strain sweep (60° C., 10 Hz, final) | | | | | | | |
| G' @ 5% strain (MPa) | 4.008 | 3.921 | 2.659 | 4.212 | 3.439 | 2.366 | 3.515 |
| G'' @ 5% strain (MPa) | 0.621 | 0.568 | 0.236 | 0.502 | 0.481 | 0.172 | 0.430 |
| tan δ @ 5% strain | 0.1548 | 0.1449 | 0.0887 | 0.1193 | 0.1399 | 0.0726 | 0.1222 |
| ΔG' (MPa) | 4.524 | 4.068 | 1.144 | 3.636 | 3.238 | 0.754 | 2.770 |
| Temp. sweep (2% strain, 10 Hz, final) | | | | | | | |
| G' (MPa) | 14.917 | 13.811 | 10.566 | 13.636 | 14.180 | 9.640 | 14.427 |
| | 7.236 | 7.235 | 5.564 | 7.133 | 6.473 | 4.450 | 6.751 |
| G'' (MPa) | 4.815 | 4.389 | 3.751 | 4.192 | 5.346 | 4.250 | 5.256 |
| | 0.938 | 0.915 | 0.562 | 0.751 | 0.788 | 0.360 | 0.785 |
| tan δ | 0.3224 | 0.3171 | 0.3545 | 0.3069 | 0.3767 | 0.4412 | 0.3643 |
| | 0.1296 | 0.1265 | 0.1010 | 0.1052 | 0.1217 | 0.0808 | 0.1162 |

TABLE 7

| Results (tan δ) of strain sweep testing @ 60° C., Examples 22-28 (carbon black) | | | | | | | |
|---|---|---|---|---|---|---|---|
| Strain (%) | 22 | 23 | 24 | 25 | 26 | 27 | 28 |
| 0.249 | 0.1045 | 0.0920 | 0.0612 | 0.0709 | 0.0972 | 0.0712 | 0.0889 |
| 0.498 | 0.1324 | 0.1010 | 0.0660 | 0.0745 | 0.1156 | 0.0745 | 0.0933 |
| 0.746 | 0.1576 | 0.1096 | 0.0704 | 0.0776 | 0.1326 | 0.0783 | 0.0982 |
| 0.994 | 0.1767 | 0.1176 | 0.0741 | 0.0811 | 0.1457 | 0.0821 | 0.1028 |
| 1.243 | 0.1908 | 0.1238 | 0.0776 | 0.0840 | 0.1559 | 0.0854 | 0.1068 |
| 1.491 | 0.2014 | 0.1290 | 0.0802 | 0.0864 | 0.1635 | 0.0883 | 0.1103 |
| 1.738 | 0.2091 | 0.1331 | 0.0827 | 0.0885 | 0.1696 | 0.0908 | 0.1132 |
| 1.990 | 0.2149 | 0.1365 | 0.0847 | 0.0903 | 0.1741 | 0.0929 | 0.1158 |
| 2.237 | 0.2193 | 0.1391 | 0.0865 | 0.0918 | 0.1775 | 0.0946 | 0.1179 |
| 2.485 | 0.2226 | 0.1412 | 0.0878 | 0.0929 | 0.1803 | 0.0961 | 0.1197 |
| 2.735 | 0.2251 | 0.1430 | 0.0890 | 0.0938 | 0.1823 | 0.0971 | 0.1213 |
| 2.983 | 0.2268 | 0.1442 | 0.0898 | 0.0945 | 0.1837 | 0.0980 | 0.1224 |
| 3.230 | 0.2282 | 0.1452 | 0.0905 | 0.0951 | 0.1847 | 0.0987 | 0.1234 |
| 3.482 | 0.2289 | 0.1460 | 0.0910 | 0.0955 | 0.1852 | 0.0992 | 0.1242 |
| 3.731 | 0.2299 | 0.1465 | 0.0915 | 0.0959 | 0.1855 | 0.0994 | 0.1247 |
| 3.983 | 0.2293 | 0.1468 | 0.0918 | 0.0960 | 0.1856 | 0.0997 | 0.1252 |
| 4.230 | 0.2291 | 0.1469 | 0.0919 | 0.0961 | 0.1854 | 0.0998 | 0.1256 |
| 4.478 | 0.2287 | 0.1471 | 0.0921 | 0.0960 | 0.1864 | 0.0999 | 0.1258 |
| 4.729 | 0.2283 | 0.1472 | 0.0921 | 0.0961 | 0.1843 | 0.0999 | 0.1260 |
| 4.976 | 0.2277 | 0.1469 | 0.0920 | 0.0960 | 0.1838 | 0.0998 | 0.1260 |
| 5.475 | 0.2264 | 0.1464 | 0.0918 | 0.0957 | 0.1826 | 0.0994 | 0.1261 |
| 5.974 | 0.2247 | 0.1459 | 0.0916 | 0.0955 | 0.1812 | 0.0990 | 0.1257 |
| 6.470 | 0.2229 | 0.1452 | 0.0913 | 0.0949 | 0.1797 | 0.0986 | 0.1254 |
| 6.968 | 0.2209 | 0.1443 | 0.0908 | 0.0945 | 0.1780 | 0.0980 | 0.1251 |
| 7.476 | 0.2188 | 0.1434 | 0.0905 | 0.0940 | 0.1762 | 0.0974 | 0.1246 |
| 7.975 | 0.2168 | 0.1425 | 0.0898 | 0.0934 | 0.1744 | 0.0969 | 0.1240 |
| 8.470 | 0.2148 | 0.1415 | 0.0893 | 0.0930 | 0.1728 | 0.0963 | 0.1235 |
| 8.970 | 0.2128 | 0.1406 | 0.0888 | 0.0925 | 0.1711 | 0.0956 | 0.1231 |
| 9.469 | 0.2109 | 0.1396 | 0.0884 | 0.0920 | 0.1694 | 0.0951 | 0.1225 |
| 9.968 | 0.2090 | 0.1387 | 0.0879 | 0.0917 | 0.1679 | 0.0946 | 0.1219 |
| 10.463 | 0.2072 | 0.1378 | 0.0874 | 0.0912 | 0.1663 | 0.0940 | 0.1214 |

TABLE 7-continued

| Results (tan δ) of strain sweep testing @ 60° C., Examples 22-28 (carbon black) | | | | | | | |
|---|---|---|---|---|---|---|---|
| Strain (%) | 22 | 23 | 24 | 25 | 26 | 27 | 28 |
| 10.956 | 0.2054 | 0.1370 | 0.0869 | 0.0907 | 0.1647 | 0.0934 | 0.1208 |
| 11.450 | 0.2036 | 0.1362 | 0.0864 | 0.0903 | 0.1631 | 0.0929 | 0.1202 |
| 11.943 | 0.2020 | 0.1353 | 0.0861 | 0.0898 | 0.1619 | 0.0924 | 0.1196 |
| 12.443 | 0.2005 | 0.1345 | 0.0857 | 0.0896 | 0.1605 | 0.0920 | 0.1192 |
| 12.941 | 0.1991 | 0.1339 | 0.0851 | 0.0892 | 0.1593 | 0.0916 | 0.1188 |
| 13.443 | 0.1976 | 0.1331 | 0.0848 | 0.0888 | 0.1580 | 0.0911 | 0.1184 |
| 13.931 | 0.1961 | 0.1323 | 0.0843 | 0.0886 | 0.1567 | 0.0907 | 0.1179 |
| 14.393 | 0.1941 | 0.1318 | 0.0840 | 0.0882 | 0.1550 | 0.0901 | 0.1172 |

TABLE 8

| Results (tan δ) of strain sweep testing @ 60° C., Examples 29-35 (silica) | | | | | | | |
|---|---|---|---|---|---|---|---|
| Strain (%) | 29 | 30 | 31 | 32 | 33 | 34 | 35 |
| 0.243 | 0.0760 | 0.0554 | 0.0635 | 0.0744 | 0.0679 | 0.0457 | 0.0664 |
| 0.499 | 0.0902 | 0.0597 | 0.0719 | 0.0907 | 0.0799 | 0.0475 | 0.0765 |
| 0.750 | 0.1028 | 0.0645 | 0.0808 | 0.1053 | 0.0926 | 0.0495 | 0.0864 |
| 1.001 | 0.1114 | 0.0689 | 0.0885 | 0.1165 | 0.1031 | 0.0522 | 0.0946 |
| 1.251 | 0.1179 | 0.0728 | 0.0946 | 0.1245 | 0.1113 | 0.0549 | 0.1008 |
| 1.502 | 0.1231 | 0.0762 | 0.0991 | 0.1303 | 0.1180 | 0.0570 | 0.1057 |
| 1.751 | 0.1269 | 0.0783 | 0.1029 | 0.1348 | 0.1224 | 0.0592 | 0.1096 |
| 2.001 | 0.1303 | 0.0807 | 0.1060 | 0.1383 | 0.1269 | 0.0611 | 0.1121 |
| 2.251 | 0.1329 | 0.0820 | 0.1083 | 0.1412 | 0.1300 | 0.0629 | 0.1147 |
| 2.500 | 0.1349 | 0.0839 | 0.1103 | 0.1437 | 0.1326 | 0.0641 | 0.1163 |
| 2.751 | 0.1366 | 0.0847 | 0.1123 | 0.1456 | 0.1346 | 0.0657 | 0.1179 |
| 3.001 | 0.1379 | 0.0858 | 0.1134 | 0.1476 | 0.1362 | 0.0671 | 0.1189 |
| 3.250 | 0.1390 | 0.0865 | 0.1147 | 0.1491 | 0.1376 | 0.0682 | 0.1197 |
| 3.503 | 0.1403 | 0.0869 | 0.1158 | 0.1501 | 0.1384 | 0.0690 | 0.1207 |
| 3.753 | 0.1415 | 0.0874 | 0.1165 | 0.1515 | 0.1395 | 0.0698 | 0.1212 |
| 4.003 | 0.1426 | 0.0877 | 0.1171 | 0.1522 | 0.1395 | 0.0704 | 0.1215 |
| 4.253 | 0.1431 | 0.0882 | 0.1178 | 0.1530 | 0.1395 | 0.0710 | 0.1218 |
| 4.503 | 0.1436 | 0.0883 | 0.1184 | 0.1539 | 0.1399 | 0.0718 | 0.1220 |
| 4.752 | 0.1443 | 0.0887 | 0.1186 | 0.1544 | 0.1398 | 0.0723 | 0.1223 |
| 5.003 | 0.1447 | 0.0887 | 0.1192 | 0.1548 | 0.1399 | 0.0726 | 0.1222 |
| 5.502 | 0.1456 | 0.0889 | 0.1194 | 0.1558 | 0.1400 | 0.0733 | 0.1222 |
| 6.001 | 0.1463 | 0.0889 | 0.1199 | 0.1564 | 0.1394 | 0.0737 | 0.1220 |
| 6.502 | 0.1468 | 0.0889 | 0.1200 | 0.1569 | 0.1387 | 0.0745 | 0.1218 |
| 7.006 | 0.1470 | 0.0888 | 0.1198 | 0.1575 | 0.1378 | 0.0744 | 0.1211 |
| 7.507 | 0.1470 | 0.0889 | 0.1199 | 0.1572 | 0.1372 | 0.0747 | 0.1207 |
| 8.008 | 0.1472 | 0.0885 | 0.1199 | 0.1572 | 0.1362 | 0.0747 | 0.1202 |
| 8.509 | 0.1471 | 0.0883 | 0.1196 | 0.1573 | 0.1358 | 0.0749 | 0.1196 |
| 9.010 | 0.1473 | 0.0882 | 0.1194 | 0.1568 | 0.1343 | 0.0749 | 0.1190 |
| 9.510 | 0.1468 | 0.0879 | 0.1191 | 0.1565 | 0.1336 | 0.0748 | 0.1183 |
| 10.011 | 0.1467 | 0.0877 | 0.1188 | 0.1559 | 0.1326 | 0.0748 | 0.1179 |
| 10.514 | 0.1464 | 0.0875 | 0.1183 | 0.1556 | 0.1318 | 0.0747 | 0.1172 |
| 11.015 | 0.1459 | 0.0871 | 0.1180 | 0.1552 | 0.1309 | 0.0747 | 0.1166 |
| 11.517 | 0.1457 | 0.0868 | 0.1177 | 0.1548 | 0.1301 | 0.0744 | 0.1157 |
| 12.018 | 0.1454 | 0.0866 | 0.1174 | 0.1541 | 0.1289 | 0.0743 | 0.1150 |
| 12.519 | 0.1449 | 0.0860 | 0.1168 | 0.1537 | 0.1280 | 0.0741 | 0.1144 |
| 13.019 | 0.1444 | 0.0860 | 0.1164 | 0.1529 | 0.1272 | 0.0739 | 0.1142 |
| 13.520 | 0.1440 | 0.0857 | 0.1160 | 0.1524 | 0.1265 | 0.0739 | 0.1132 |
| 14.026 | 0.1435 | 0.0854 | 0.1155 | 0.1518 | 0.1257 | 0.0735 | 0.1127 |
| 14.526 | 0.1432 | 0.0851 | 0.1151 | 0.1511 | 0.1250 | 0.0733 | 0.1119 |

That which is claimed is:

1. A method of making a functionalized random interpolymer, said interpolymer comprising polyene and styrenic mer units, said method comprising (a) in a reaction vessel that contains ingredients which comprise a non-polar solvent, a polar coordinator compound, and unsaturated monomers that comprise one or more polyenes and a sufficient amount of one or more hydrocarbon styrenes so as to provide about 20 to about 40% of the constituent mer units of said interpolymer, initiating polymerization of said unsaturated monomers with an effective amount of an initiating compound having the general formula

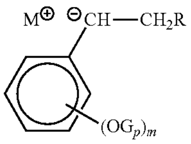

where

M is an alkali metal atom,

R is a hydrocarbyl group, each $G_p$ independently is a protecting group, and m is an integer of from 2 to 5 inclusive, and (b) hydrolyzing each of said protecting groups by reaction with tetrabutylammonium fluoride, thereby providing said functionalized random interpolymer.

2. The method of claim 1 wherein said one or more polyenes comprises at least one diene.

3. The method of claim 1 wherein said one or more polyenes comprises at least one conjugated diene.

4. The method of claim 1 wherein a portion of said unsaturated monomers is added to said reaction vessel after initiation of said polymerization.

5. The method of claim 4 wherein at least one of said initiating compound and said unsaturated monomers is added to said reaction vessel continuously.

6. The method of claim 1 wherein said reaction vessel is maintained at a temperature of at least 70° C.

7. The method of claim 1 wherein said initiating compound is provided by reacting equimolar amounts of a hydrocarbyl alkali metal compound with a styrenic compound having the general formula

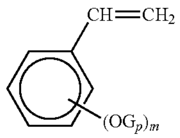

where each $G_p$ independently is a protecting group, and m is an integer of from 2 to 5 inclusive.

8. The method of claim 3 wherein said random interpolymer has a number average molecular weight of from about 103,000 to about 165,000 g/mol.

9. A method of making a functionalized random interpolymer, said interpolymer comprising conjugated diene and styrenic mer units, said method comprising (a) in a reaction vessel that contains ingredients which comprise a non-polar solvent, a polar coordinator compound, and unsaturated monomers that comprise one or more conjugated dienes and a sufficient amount of one or more hydrocarbon styrenes so as to provide about 20 to about 40% of the constituent mer units of said interpolymer, initiating polymerization of said unsaturated monomers with an effective amount of an initiating compound having the general formula

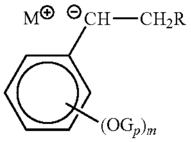

where

M is an alkali metal atom,

R is a hydrocarbyl group, each $G_p$ independently is a protecting group, and m is an integer of from 1 to 5 inclusive, with the proviso that, when m=1, the ($OG_p$) substituent is para the M-containing substituent, thereby providing a random interpolymer having a number average molecular weight of from about 103,000 to about 165,000 g/mol, and (b) hydrolyzing each of said protecting groups by reaction with tetrabutylammonium fluoride, thereby providing said functionalized random interpolymer.

10. The method of claim 9 wherein a portion of said unsaturated monomers is added to said reaction vessel after initiation of said polymerization.

11. The method of claim 10 wherein at least one of said initiating compound and said unsaturated monomers is added to said reaction vessel continuously.

12. The method of claim 9 wherein said reaction vessel is maintained at a temperature of at least 70° C.

13. The method of claim 9 wherein said initiating compound is provided by reacting equimolar amounts of a hydrocarbyl alkali metal compound with a styrenic compound having the general formula

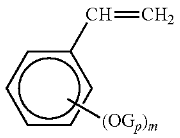

where each $G_p$ independently is a protecting group, and m is an integer of from 1 to 5 inclusive, with the proviso that, when m=1, the ($OG_p$) substituent is para the vinyl group.

14. The method of claim 9 wherein m is 2.

* * * * *